United States Patent [19]

Stephens et al.

[11] Patent Number: 4,753,802

[45] Date of Patent: Jun. 28, 1988

[54] VERAPAMIL DOSAGE FORM

[75] Inventors: Sally I. Stephens, Mt. View; L. G. Hamel, Sunnyvale, both of Calif.

[73] Assignee: Alza Corporation, Palo Alto, Calif.

[21] Appl. No.: 841,144

[22] Filed: Mar. 19, 1986

[51] Int. Cl.⁴ .................. A61K 9/22; A61K 9/24; A61K 9/44
[52] U.S. Cl. ..................................... 424/467; 424/473
[58] Field of Search .............................. 424/467, 473

[56] References Cited

U.S. PATENT DOCUMENTS 4,627,850 12/1986 Deters et al. .................. 424/457
4,681,583 7/1987 Urquhart et al. ............... 424/453

Primary Examiner—Shep K. Rose
Attorney, Agent, or Firm—Paul L. Sabatine; Edward L. Mandell; Shelley G. Precivale

[57] ABSTRACT

An osmotic dosage form comprising verapamil and mannitol in a nonequilibrium ratio.

11 Claims, 1 Drawing Sheet

VERAPAMIL DOSAGE FORM

FIELD OF THE INVENTION

This invention pertains to both a novel and useful dosage form comprising the beneficial drug verapamil for administering it to a recipient.

BACKGROUND OF THE INVENTION

Verapamil is an ionic calcium influx inhibitor more commonly known as a calcium channel blocking agent. The principal pharmacologic and physiologic action of verapamil is to inhibit the transmembrane influx of extracellular calcium ions across the membrane of myocardial cells and vascular smooth muscle cells. By inhibiting calcium influx, verapamil inhibits the contractile processes of cardiac and vascular smooth muscles, thereby dilating the main coronary and systemic arteries. The drug is indicated and approved by the Food and Drug Administration for the management of unstable or chronic stable angina pectoris for the treatment of supraventricular tachyarrhythmias, and for the temporary control of rapid ventricular rate in arterial flutter or atril fibrillation.

Verapamil is administered generally as its pharmaceutically acceptable addition salt. Orally administered verapamil is absorbed from the gastrointestinal tract. The prior art administers verapamil orally for the indicated cardiovascular indications in tablet form. Currently, verapamil is administered orally as tablets three or four times daily. While these conventional tablet forms are used for the indicated therapy, a fundamental limitation common to tablets is their temporal pattern of drug delivery. That is, they give up their drug to surrounding tissues and fluids at varying rates that are highest initially and then declines continually thereafter. For a therapeutically important cardiovascular drug such as verapamil, this sawtooth pattern of delivery of high-dose, low-dose variation of the needed drug presents drug to the tissues and then denies drug to the tissues, leading to unacceptable therapy. Also, within the intervals between doses, and with longer intervals between doses, there is a greater amplitude of the dosage cycle leading to irregularity of drug bioavailability and uncontrolled therapy.

It is apparent from the above presentation to a person having ordinary skill in the art to which the present subject matter pertains, that an urgent need exists for a dosage form for administering verapamil at a programmed rate for a prescribed period of time. The need exists for a dosage form that delivers verapamil at a controlled rate over a prolonged period of time for substantially eliminating the disadvantages known to the prior art.

OBJECTS OF THE INVENTION

Accordingly, in view of the above presentation, it is an immediate object of this invention to provide a dosage form for administering verapamil that substantially overcomes the disadvantages known to the prior art.

Another object of the invention is to provide a dosage form for the controlled and continuous administration of verapamil over a prolonged period of time, the use of which requires intervention only for initiation of the therapeutic regimen.

Another object of the invention is to provide a dosage form that delivers verapamil at a rate controlled by the dosage form throughout the day with once and sometimes twice daily dosing of the dosage form.

Another object of the invention is to provide a dosage form for delivering verapamil, the use of which reduces the frequencies of dosage required by the prior art.

Another object of the invention is to provide a novel dosage form adapted for the patient's convenience and enables patent compliance for executing a prescribed therapeutic program.

Another object of the invention is to provide an osmotic dosage form comprising verapamil and mannitol both present in the dosage form in a nonequilibrium ratio, and which verapamil and mannitol are dispensed from the dosage form in a corresponding ratio.

Another object of the invention is to provide an osmotic dosage form containing a composition comprising verapamil and mannitol in a nonequilibrium ratio and a gel member for maintaining the nonequilibrium ratio of the components of the composition.

Another object of the invention is to provide an osmotic dosage form housing a composition comprising verapamil and mannitol and a gel member for essentially preventing spurious burst of composition from the dosage form.

Another object of the invention is to provide an osmotic dosage form comprising at least two passageways position on spaced apart surfaces of the dosage form, and which device houses a gel member for substantially preventing fluid convection from one passageway through the dosage form to a distant and different passageway.

Another object of the invention is to provide an osmotic dosage form comprising at least two spaced apart passageways, a compartment comprising verapamil, mannitol and a gel member that substantially prevents fluid flow through the passageways and the compartment, thereby substantially preventing fluid washout of verapamil and mannitol from the dosage form.

Other objects, features and advantages of the invention will be more apparent to those versed in the art from the following specification, taken in conjunction with the drawings and the accompanying claims.

BRIEF DESCRIPTION OF THE DRAWING

In the drawing figures, which are not drawn to scale, but are set forth to illustrate various an embodiment of the invention the drawing figures are as follows.

In the drawings and in the specification, like parts are identified by like numbers. The terms appearing earlier in the specification and in the description of the drawing figures, as well as embodiments thereof, are further described elsewhere in the disclosure.

DETAILED DESCRIPTION OF THE DRAWINGS

Figure 1:
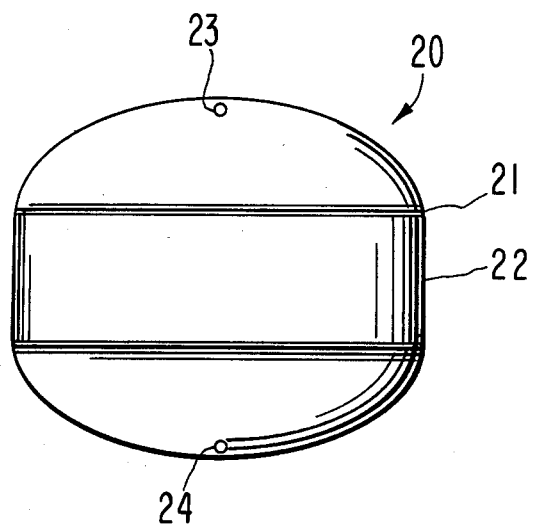
FIG. 1 is a partial view of an osmotic dosage form shaped and sized for orally administering the beneficial drug verapamil to the gastrointestinal tract over a prolong period of time; and, FIG. 2 is a partially opened view of the dosage form of FIG. 1 with a part of the exterior wall of the dosage form sectioned for illustrating the structure of the dosage form.
Figure 2:
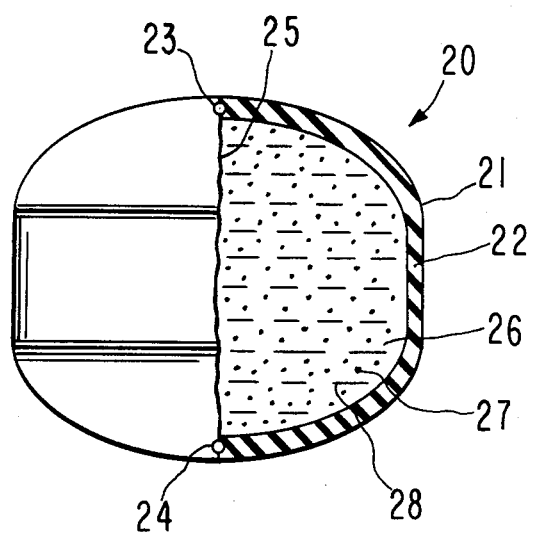

Turning now to the drawing figures in detail, which drawing figures are an example of the dosage form provided by the invention, and which example is not to be considered as limiting, one example is the dosage form, manufactured as an osmotic device, as illustrated in FIGS. 1 and 2 and designated by the numeral 20. In FIG. 1, osmotic dosage form 20 comprises a body member 21 comprising a wall that surrounds and forms an internal compartment, not seen in FIG. 1. Dosage form 20 comprises at least one exit passageway 23, and more preferably at least two passageways 24 for connecting the interior of dosage form 20 with the exterior, biological environment of use.

In FIG. 2, osmotic dosage form 20 is seen in opened view with wall 22 sectioned at 25. In FIG. 2, dosage form 20 comprises body 21, wall 22 that surrounds and defines an internal compartment 26, and a first passageway 23 and a second passageway 24, for dispensing the contents of compartment 26 from dosage form 20.

Wall 22 of dosage form 20 comprises totally, or in at least a part, a composition that is permeable to the passage of an exterior fluid present in the environment of use, and it is substantially impermeable to the passage of verapamil and other ingredients present in compartment 26. Semipermeable wall 22 of device 20 is substantially inert, that is, it maintains its physical and chemical integrity during the dispensing life of dosage form 20. The phrase, "maintains its physical and chemical integrity" means wall 22 does not lose its structure and it does not change during the dispensing life of dosage form 20. Wall 22 is formed of a composition comprising cellulose acetate having an acetyl content of 39.8%, cellulose acetate having an acetyl content of 32%, hydroxypropylcellulose, and polyethylene glycol 3350. In one presently preferred embodiment, wall 22 is formed of a composition that comprises from 50 to 55 weight percent cellulose acetate having an acetyl content of 39.8%, from 15 to 20 weight percent of cellulose acetate having an acetyl content of 32%, from 22 to 27 weight percent hydroxypropylcellulose and from 3 to 8 weight percent polyethylene glycol 3350, with the total amount of the wall forming members equal to 100 weight percent. A more specific wall forming composition comprises 52.5 wt % (weight percent) cellulose acetate having an acetyl content of 39.8%, 17.5 wt % cellulose acetate having an acetyl content of 32%, 25 wt % hydroxypropylcellulose, and 5 wt % polyethylene glycol. In another presently preferred embodiment wall 22 comprises from 33 to 38 wt % cellulose acetate having an acetyl content of 39.8%, 33 to 38 wt % cellulose acetate having an acetyl content of 32%, 22 to 28 wt % hydroxypropylcellulose, and 3 to 8 wt % polyethylene glycol 3350, with the total amount of the wall forming members equal to 100 wt %. A more specific wall forming composition comprises 35 wt % cellulose acetate having an acetyl content of 39.8%, 35 wt % cellulose acetate having an acetyl content of 32%, 25 wt % hydroxypropylcellulose, and 5 wt % polyethylene glycol.

Internal compartments 26 of dosage form 20 houses a dispensable composition comprising the beneficial drug verapamil 27, identified by dots, and other composition forming members including mannitol, polyethylene oxide, polyvinylpyrrolidone and stearic acid or magnesium stearate. The drug verapamil 27 is present in a presently preferred embodiment as its pharmaceutically acceptable addition salt, such as verapamil hydrochloride. Verapamil hydrochloride exhibits a solubility of 527 mg/ml at 37° C. The osmotic pressure of a saturated aqueous solution of verapamil hydrochloride at 37° C. is 11 atmospheres, atm, as measured by vapor pressure osmometry. These properties of verapamil, its low osmotic pressure and its high solubility in aqueous solution including biological fluids, are unacceptable for delivering verapamil from an osmotic dosage form. The present invention sought to unexpectedly enhance the delivery properties of verapamil by formulating verapamil with osmotic solutes at their equilibrium ratios. The formulation data showed osmotic solutes such as organic acids gave unacceptable high solubilities, while osmotic solutes such as inositol resulted in an insufficient cumulative amount of verapamil released over time. The results of the formulation are given in the accompanying table. In the table, $S_D$ is the solubility of verapamil, $S_o$ is the solubility of the osmotic solute, $S_T$ is the total solubility of $S_D$ and $S_o$ in a common aqueous fluid, and $\pi$ is the osmotic pressure of the blend of $S_D$ plus $S_o$. The formulation measurements set forth in the table indicate the high solubility of verapamil unexpectedly depressed in the presence of mannitol, and concomitantly the osmotic pressure of verapamil is raised in the presence of mannitol. Moreover, the invention enhances the operability of the osmotic dosage form by providing a nonequilibrium ratio of 0.9 to 1.1 manitol to verapamil, preferably 1.0 with an unexpected accompanying decrease in the dimensions of the dosage form.

Prior to this invention, a drug and its accompanying osmagent are present in an osmotic dosage form in an equilibrium ratio. An equilibrium ratio is defined as the ratio of the concentration in mg/ml for a saturated solution of osmagent divided by the concentration in mg/ml of a saturated solution of drug with both components present in a common solution. A drug and an osmagent are in an equilibrium ratio to assure constancy of osmotic pressures and concentration of both components, particularly of the drug, in the dosage form and during administration of the drug throughout the functional life of the dosage form. When an osmagent and a drug are in nonequilibrium ratio, then the soluble components are still delivered in equilibrium ratio, the most soluble of either the drug or the osmagent is preferentially extracted and delivered from the dosage form. This physical-chemical action leads to a declining and unpredictable release pattern of drug from the dosage form. Such a dosage form comprising a nonequilibrium compartment does not lend itself to the practice of acceptable medical therapy. A nonequilibrium ratio is the ratio of osmagent to drug concentration that is substantially higher or lower than the equilibrium ratio.

TABLE

| Drug or Osmotic Solute | $S_d(370)$ (mg/ml) | $S_o$ (mg/ml) | $S_T$ (mg/ml) | $\pi$ (atm) |
|---|---|---|---|---|
| Verapamil-HCl | 527 | | | 10.9 |
| | 74(at 21° C.) | | | |
| in AGF | 408 | | | 13.0 |
| in AIF | 340 | | | 13.3 |
| in Saline | 140 | | | — |
| Mannitol | 150 | 219 | 369 | 42.8 |
| Disodium Succinate | 629 | 117 | 746 | 36.6 |
| Tartaric Acid | 243 | 726 | 969 | |
| Sodium Chloride | .12 | 209 | 209 | |
| Sodium Sulfate | .12 | 411 | 411 | |
| D-Galactose | 38 | 457 | 495 | 87.1 |
| Succinic Acid | 675 | 113 | 788 | 22.9 |
| Adipic Acid | 715 | 67 | 782 | 13.9 |
| L-Arabinose | 51 | 473 | 524 | 110.3 |
| Sodium Tartrate | 48 | 327 | 375 | 100.0 |
| Ascorbic Acid | 558 | 145 | 703 | 76.8 |
| Mannitol/ | 441 | 132 | 573 | 65.8 |
| Succinic Acid | | | | |
| Fumaric Acid | 572 | 77 | 649 | 21.4 |
| Malic Acid | 384 | 436 | 820 | |
| Guaifenesin | 783 | 81 | 864 | |
| Inositol | 151 | 122 | 273 | 20.6 |

TABLE-continued

| Drug or Osmotic Solute | $S_d(370)$ (mg/ml) | $S_o$ (mg/ml) | $S_T$ (mg/ml) | $\pi$ (atm) |
|---|---|---|---|---|
| Insulin | 147 | 50 | 197 | |

The amount of verapamil present in an osmotic dosage form, and the amount of mannitol present in an osmotic dosage form having a nonequilibrium ratio of $1\pm0.1$ is from 50 mg to 600 mg. More preferably from 110 mg to 250 mg of verapamil and from 110 to 250 mg of mannitol. In a presently preferred embodiment, a dosage form comprises 120 mg of verapamil and 120 mg of mannitol, or in another embodiment the dosage form comprises 240 mg of verapamil and 240 mg of mannitol. In the embodiment wherein the dosage form comprises 120 mg of verapamil and 120 mg of mannitol, the dosage form includes also 2 to 4 mg of polyethylene oxide, 4 to 6 mg of a member selected from the group consisting of stearic acid or magnesium stearate, and 4 to 6 mg of polyvinylpyrrolidone. In the embodiment wherein the dosage form comprises 240 mg of verapamil and 240 mg of mannitol, the dosage form comprises also 4 to 6 mg of polyethylene oxide, 9 to 12 mg of polyvinylpyrrolidone, and 9 to 12 mg of a member selected from the group consisting of stearic acid and magnesium stearate. The composition present in a nonequilibrium ratio is dispensed through the passageway in its nonequilibrium ratio to the environment of use.

The expression "exit means" as used herein comprises means and methods suitable for dispensing the beneficial drug verapamil from the dispensing device. The means include at least one passageway or orifice that passes through wall 22 for communicating verapamil 27 in compartment 26 with exterior of dosage form 20. The expression "at least one passageway" includes aperture, orifice, bore, pore, porous element through which verapamil can migrate, a hollow fiber, capillary tube, and the like. The expression includes also a material that erodes or is leached from wall 22 in the fluid environment of use to produce at least one passageway of controlled releasing dimensions in the device. Representative materials suitable for forming at least one passageway, or two passageways, include an erodible poly(glycolic) or poly(lactic) acid member in the wall, a gelatinous filament, poly(vinyl alcohol), leachable materials such as fluid removable pore forming polysaccharides, salts or oxides, and the like. A passageway or a plurality of passageways can be formed by leaching a material such as sorbitol from the wall. The passageway can have any shape, such as round, triangular, square, elliptical, irregular, and the like. The device can be constructed with one or more passageways in a spaced apart relation on more than a single distant surface of a dosage form. Passageways, and equipment for forming passageways are disclosed in U.S. Pat. Nos. 3,916,889; 4,063,064; and 4,088,864. Representative passageways formed by governed leaching to produce a pore of pre-controlled size are disclosed in U.S. Pat. No. 4,200,098.

The osmotic dosage form of the invention is manufactured by standard manufacturing techniques. For example, the compartment forming ingredients are formulated by wet granulation technique using an organic solvent or cosolvent, such as denatured alcohol as the granulating fluid. The ingredients forming the compartment in one manufacture comprising verapamil hydrochloride, mannitol and polyethylene oxide are individually passed through a 40 mesh screen and then thoroughly blended in a mixer. Next, polyvinylpyrrolidone is dissolved in a portion of the granulation fluid, the cosolvent described immediately above. Then, the polyvinylpyrrolidone solution is slowly added to the dry powder with continual mixing in a blender. The granulating fluid is added until a wet blend is achieved, generally about 400 cc of granulating fluid per kilogram of blend. The wet mass blend is then forced through a 20 mesh screen onto oven trays and dried for 18 to 24 hours at 50° C. The dried granules are then sized with a 20 mesh screen. Next, stearic acid is passed through on 80 mesh screen and added to the dry, screened granular blend. The granulation is then put into milling jars and mixed on a jar mill for 10 to 15 minutes.

The composition forming blend is then compressed using a tablet press. In one manufacture a 4-station press can be used. The speed of the press is set at 18 rpm and the maximum load set at 2.8 tons. Two dosage forms are tableted using the press, one using a 13/32 inch (10.32 mm) round, standard concave punch, and the other using a 5/16 inch (7.94 mm) round standard concave punch.

The wall of the osmotic dosage form can be formed in one technique using the air suspension procedure. This procedure consists in suspending and tumbling the drug forming compartment in a current of air and a wall forming, composition until the wall is applied to the drug forming compartment. The air suspension procedure is well-suited for independently forming the wall. The air suspension procedure is described in U.S. Pat. No. 2,799,241; in *J. Am. Pharm. Assoc.*, Vol. 48, pages 451 to 459, 1959; and ibid, Vol. 49, pages 82 to 84, 1960. Osmotic dosage forms can be also coated with the wall-forming composition in a Wurster® air suspension coater, using a methylene dichloride/methanol cosolvent, 80/20, w/w, using 2.5 to 4% solids. The Aeromatic® air suspension coater using a methylene dichloride/methanol cosolvent, 87/13 w/w, also can be used for applying the wall. Other wall forming techniques such as pan coating can be used for providing the dosage form. In the pan coating system, wall forming, or lamina forming compositions are deposited by successive spraying of the compositions on the verapamil accompanying by tumbling in a rotating pan. A pan coater is used to produce thicker walls. A larger volume of methanol can be used in a cosolvent to produce a thinner wall. Finally, the wall coated compartments are dried in a forced air oven at 50° C. for several hours to free the dosage form of solvent. Generally, the wall formed by these techniques will have a thickness of 2 to 20 mils with a presently preferred thickness of 4 to 10 mils.

Exemplary solvent suitable for manufacturing the wall include inert inorganic and organic solvent do not adversely harm the wall, the verapamil, and the final dosage form. The solvents broadly include members selected from the group consisting of alcohols, ketones, esters, ethers, aliphatic hydrocarbons, halogenated solvents, cycloaliphatic solvents, aromatic, heterocyclic, aqueous, and mixtures thereof.

Following the procedure of the invention a number of dosage forms were prepared for dispensing the drug verapamil. The dosage forms were prepared as follows: first, the following compartment forming ingredients were individually sized through a 40 mesh screen, 2,850 g of verapamil hydrochloride, 2,850 g of mannitol powder and 60 g of polyethylene oxide having a molecular weight of 5,000,000. Then, the three screened ingredients were placed in a commercial blender and homogeneously blended for 5 minutes. Next, 120 g of polyvinylpyrrolidone and 1,930 ml of ethyl alcohol denatured were added to a mixing vessel and blended for 12 minutes, until all the solid dissolved in the ethyl alcohol. This liquid mixture was slowly added to the blend comprising the three dry ingredients until granulation was obtained, usually by blending for 20 minutes. The wet granulation was sized through a 10 mesh screen, and the granules spread out on an oven tray and placed in an oven at 50° C. for 18 hrs. The dried granules were sized through a 10 mesh, and 115 g of stearic acid, previously forced through a 40 mesh screen was added to the dried granules, and all the granulation mixed in a V-blender for 8 minutes.

Next, 1,965 g of the just prepared granulation was tabletted on a press and a number of compartment forming compositions were prepared with a 5/16 inch round-shaped punch and die. The press comprised 4 stations, had a compression speed of 18 rpm and a compression load of 2.8 tons. The compressed compartment forming cores had an average weight of 257.2 mg comprising 120 mg of verapamil hydrochloride, and an average hardness of 9.7 kp.

Next, 3,954 g of the verapamil hydrochloride granulation was added to the press and a number of compartment forming compositions comprising 240 mg of verapamil hydrochloride prepared using a 13/32 inch round-shaped punch & die. The composition was compressed under a compression load of 2.25 tons. The final composition had an average weight of 509.6 mg and exhibited an average hardness of 8.9 kp.

Then, the compressed compositions comprising 120 mg of verapamil hydrochloride was surrounded with a wall. The wall was formed from a composition comprising 1,755 ml of methylene chloride; 735 ml of methanol; 47.25 g of cellulose acetate having an acetyl content of 39.8%; 15.75 g of cellulose acetate having an acetyl content of 32%; 22.5 g of hydroxypropyl cellulose; and 4.5 g of polyethylene glycol 3350, that was prepared by mixing all the ingredients in a stainless steel vessel until all the solids were dissolved. The compressed composition were placed in an Aeromatic ® Coater, and the coating solution pumped at a rate of 20 ml/min until each system gained an average 15.6 mg wall. Next, the coated systems were placed on oven trays, placed in a relative humidity (R. H.) chamber, at 50° C. and 50% R. H. for 45 to 50 hrs. The systems were than transferred to a forced air oven and dried for 20 to 25 hrs at 50° C. The final systems had an average weight of 272.7 mg, and an average dry wall weight of 14.9 mg.

The compressed compositions comprising 240 mg of verapamil hydrochloride were surrounded with a wall in a like manner. The wall forming composition comprised 3% solids, and the composition comprised 2,340 ml of methylene chloride; 980 ml of methanol; 42 g of cellulose acetate having an acetyl content of 39.8%; 42.0 g of cellulose acetate having an acetyl content of 32%; 30 g of hydroxypropyl cellulose; and, 6 g of polyethylene glycol 3350.

The compressed compositions were coated in a Hi-Coater ®, with the coating solution pumped at a rate of 35 ml/min until each composition was surrounded with a 28 mg wall. The systems were dried in a relative humidity chamber at 50° C. and 50% R. H. for 45 to 50 hrs, and then in a forced air oven at 50° C. for 50 hrs.

The average weight of dried dosage form was 535.7 mg, with a wall having an average dry weight of 25.2 mg.

In both of the above manufactures, the dosage forms were drilled on two distant surfaces to produce on each surface a 10 mil passageway through the wall. The final composition for the first manufactured dosage form was as follows: verapamil hydrochloride 47.5 wt % (122.5 mg); mannitol 47.5 wt % (122.5 mg); polyethylene oxide coagulant 1 wt % (2.6 mg); polyvinypyrrolidone 2 wt % (5.2 mg); a wall comprising cellulose acetate with an acetyl content of 39.8%, 52.5 wt % (8.2 mg); cellulose acetate having an acetyl content of 32%, 17.5 wt % (2.7 mg); hydroxypropyl cellulose 25 wt % (3.9 mg); and polyethylene glycol 3350, 5 wt % (0.8 mg). The dosage form had an average rate of release of 7.1 to 7.7 mg/hr in artificial gastric fluid and in artificial intestinal fluid over a 15 to 17 hr. release period.

The final composition of the second dosage forms was as follows: verapamil hydrochloride 47.5 wt % (242.5 mg); mannitol 47.5 wt % (242.5 mg); polyethylene oxide 1 wt % (5.1 mg); polyvinylpyrrolidone 2 wt % (10.2 mg) and stearic acid 2 wt % (10.2 mg); and a wall comprising cellulose acetate having an acetyl content of 39.8%, 25 wt % (9.9 mg); cellulose acetate having an acetyl content of 32%, 35 wt % (9.9 mg); hydroxypropyl cellulose 25 wt % (7.1 mg); and polyethylene glycol 3350, 5 wt % (1.4 mg). The dosage forms had an average rate of release of 13.1 to 13.6 mg/hr in artificial gastric fluid and in artificial intestinal fluid over a total release life of 17.8 to 20.2 hrs.

In summary, it will be appreciated that the present invention contributes to the delivery art an unobvious dosage form that possess practical utility. While the invention has been described and pointed out in details with reference to operative embodiments thereof, it will be understood that those skilled in the art will appreciate that various changes, modifications, substitutions and omissions can be made without departing from the spirit of the invention. It is intended therefore, that the invention embraces those equivalents within the scope of the claims which follow.

We claim:

1. A dosage form for delivering the beneficial drug verapamil to a biological environment of use, the dosage for comprising:
   (a) a wall comprising in at least a part a composition comprising a cellulose acylate, which wall is permeable to the passage of fluid, impermeable to the passage of verapamil, and surrounds and forms:
   (b) a compartment;
   (c) a dosage amount of verapamil in the compartment, with the proviso that said verapamil is present with mannitol in the compartment in a nonequilibrium ratio of 0.9 to 1.1; and,
   (d) at least one passageway in the wall connecting the compartment with the exterior of the dosage form for dispensing verapamil to the environment of use over time.

2. The dosage form for delivering the beneficial drug verapamil according to claim 1, wherein verapamil is present as a therapeutically acceptable addition salt.

3. The dosage forms for delivering the beneficial drug verapamil according to claim 1, wherein verapamil is present in the dosage form as verapamil hydrochloride.

4. The dosage form for delivering the beneficial drug verapamil according to claim 1, wherein the cellulose acylate is cellulose acetate having an acetyl content of 39.8%.

5. The dosage form for delivering the beneficial drug verapamil according to claim 1, wherein the cellulose acylate is cellulose acetate having an acetyl content of 32%.

6. The dosage form for delivering the beneficial drug verapamil according to claim 1, wherein wall composition comprises a cellulose acylate having an acetyl content of 39.8% and a cellulose acylate having an acetyl content of 32%.

7. The dosage form for delivering the beneficial drug verapamil according to claim 1, wherein the nonequilibrium ratio is 1.

8. The dosage form for delivering the beneficial drug verapamil according to claim 1, wherein the dosage form comprises from 50 to 600 mg of verapmil.

9. The dosage form for delivering the beneficial drug verapamil according to claim 1, wherein the dosage form comprises from 115 to 125 mg of verapamil pharmaceutically acceptable salt.

10. The dosage form for delivering the beneficial drug verapamil according to claim 1, wherein the dosage form comprises 235 to 245 mg of verapamil pharmaceutically acceptable salt.

11. The dosage form for delivering the beneficial drug verapamil according to claim 1, wherein the environment of use in the gastrointestinal tract, and the dosage form is adapted for oral admittance into said environment of use.

* * * * *